United States Patent [19]

Parrott

[11] Patent Number: 6,086,887
[45] Date of Patent: Jul. 11, 2000

[54] ANTIPERSPIRANT OR DEODORANT

[75] Inventor: David Terence Parrott, Bebington, United Kingdom

[73] Assignee: Helene Curtis, Inc., Chicago, Ill.

[21] Appl. No.: 09/196,817

[22] Filed: Nov. 20, 1998

[30] Foreign Application Priority Data

Nov. 24, 1997 [GB] United Kingdom .................... 9724802

[51] Int. Cl.⁷ ..................................................... A01N 65/00
[52] U.S. Cl. ........................................................... 424/195.1
[58] Field of Search ............................................ 424/195.1

[56] References Cited

U.S. PATENT DOCUMENTS 5,445,822  8/1995  Bracco .

FOREIGN PATENT DOCUMENTS

| | | |
|---|---|---|
| 173478 | 3/1986 | European Pat. Off. . |
| 310252 | 4/1989 | European Pat. Off. . |
| 0330140 | 8/1989 | European Pat. Off. . |
| 416855 | 3/1991 | European Pat. Off. . |
| 2604624 | 4/1988 | France . |
| 2704390 | 11/1994 | France . |
| 2271928 | 4/1994 | United Kingdom . |
| 90/07331 | 7/1990 | WIPO . |
| 98/33476 | 8/1998 | WIPO . |

OTHER PUBLICATIONS

International Search Report Application No. PCT/EP 98/07535 mailed Apr. 21, 1999.

Ralf Dieter Merkle: Ole in der Kosmetic Sofw:Seifen, Ole, Fette, Wachse Journal, vol. 118, No. 16, Oct. 1992, pp. 991–999.

*Primary Examiner*—Herbert J. Lilling
*Attorney, Agent, or Firm*—Matthew Boxer

[57] ABSTRACT

Deodorant and antiperspirant compositions can suffer from perceived irritancy when applied topically, which can be ameliorated or overcome by incorporating within the composition borage seed oil, and especially an amount selected in the range of from 0.5 to 10 wt %. The compositions advantageously comprise an aluminium or aluminium-zirconium active.

7 Claims, No Drawings

ANTIPERSPIRANT OR DEODORANT

The invention relates to antiperspirant or deodorant compositions. In particular it relates to antiperspirant or deodorant compositions comprising borage seed oil.

The antiperspirant market is dominated with products based on aluminium or zirconium salts which are intended to prevent, or at least control, perspiration at the skin surface, particularly on the underarm, whilst often simultaneously providing a perceived degree of deodorancy.

In contrast, deodorants are formulations which are designed to either mask malodour or prevent its formation by reducing the local micro-organism population.

Antiperspirant and deodorant compositions are utilised in many product forms e.g. roll-ons, creams, sticks, aerosols and pump sprays. However all forms suffer from a number of common disadvantages.

A principal disadvantage of many deodorants and antiperspirants is their perceived skin unfriendliness. More particularly, the presence of volatile carriers such as volatile silicones and ethanol, and indeed deodorant and antiperspirant actives as well as a host of other ingredients commonly employed in deodorant and antiperspirant formulations is perceived to have an adverse effect, in particular on irritant effect, on a user's skin following application. Irritation can be ameliorated by lowering the amount of an active ingredient in the composition or by reducing the active's penetration through the skin A serious drawback of both approaches is that the efficacy is impaired.

Adverse effects deter many consumers from utilising deodorants and antiperspirants thereby depriving the consumer of the benefits to be derived from such cosmetics.

An object of the invention is to provide such a composition which has excellent antiperspirant or deodorant efficacy, excellent cosmetic properties and aesthetics with reduced or no irritation.

European Patent Application 0416855 (Efamol) discloses treatment of skin damage due to radiotherapy with gamma linolenic acid (GLA) and also teaches a variety of suitable plant sources of GLA, including Borage species. PCT application WO 90/07331 (Went) teaches treatment of inflammation arising from arthritis or headache by topical application of GLA; borage seed is taught as a suitable source. European Patent Application 0173478 (Efamol) discloses treatment of inflammatory skin disorders with compositions containing GLA and glucocorticoids; borage species such as *Borago officinalis* is mentioned as a rich source of GLA. French patent 2,704,390 (Boiron) discloses an oral supplement containing borage seed oil to provide anti-aging benefits to skin. French patent 2,604,624 (Parfums Rochas) discloses skin care compositions containing polyunsaturated carboxylic acids, such as GLA; borage is said to be rich in GLA. U.S. Pat. No. 5,445,822 (Bracco) discloses cosmetic compositions containing polyunsaturated acids such as GLA.

Great Britain Patent 2,271,928 (Laing) discloses the use of borage family plant extracts for alleviation of skin disorders and irritations.

Tollesson et al., "Transepidermal Water Loss and Water Content in the Stratum Corneum in Infantile Sebhorroeic Dermatitis", Acta Derm Venereol (Sweden), February 1993, 73 (1), p. 18–20, disclose the use of topically applied borage oil for treatment of sebhorroeic dermatitis. Bahmer et al., "Treatment of Atopic Dermatitis with Borage Seed Oil (Glandol)—A Time Series Analytic Study", Kinderarztl Prax (Germany), October 1992, 60 (7), p. 199–202, disclose the use of borage oil for the treatment of atopic dermatitis.

The art does not teach the use of GLA or borage seed oil to reduce irritation or sting associated with the use of deodorants or antiperspirants. We that among GLA containing plant sources borage seed oil was particularly effective at ameliorating irritation and that this effect could not be attributed merely to the presence of GLA in the borage seed oil. We also found that borage seed oil was more effective than other, non-GLA-containing anti irritants.

Surprisingly, we have found that borage seed oil can be incorporated into an antiperspirant or deodorant cosmetic composition to produce a composition which has improved and attractive cosmetic characteristics expected of such compositions as well as excellent efficacy, low irritation potential and non-stinging upon application.

According to the invention there is provided an antiperspirant or deodorant cosmetic composition suitable for topical application to the human skin, comprising:
 i. an antiperspirant or deodorant active;
 ii. a carrier for the antiperspirant or deodorant active; and
 iii. borage seed oil.
Where the formulation is an antiperspirant it commonly comprises 1–35% by weight of the composition of an antiperspirant active.

Borage seed oil is obtained from the seeds of borage plant, also known as *Borago officinalis L.* (Boraginaceae), which is an herbaceous annual plant, native to Europe, Asia Minor and North Africa, naturalized in the United States. The seed oil contains: gamma-linolenic acid (GLA), ~24%, sterols (e.g., campestrol and sitosterol), tocopherols, linoleic acid (~38%), oleic acid (~14.5–23%), palmitic (~4.7%), amabiline, etc. See Whipkey et al., "In Vivo and In Vitro Lipid Accumulation in *Borago officinalis L.* ", JAOCS, 65 (6), 979–984 (1988); and Leung et al., "Encyclopedia of Common Natural Ingredients Used in Food, Drugs and Cosmetics", 2nd ed., John Wiley & Sons, Inc., New York (1996).

Borage seed oil is employed according to the present invention to reduce or eliminate the skin irritation and/or sting caused by co-components of the antiperspirant or deodorant composition according to the invention.

The amount of borage seed oil in the inventive compositions ranges generally from at least 0.05%, preferably from 0.1% to 20%, most preferably from 0.5% to 10%. In some compositions it is convenient to employ a concentration of up to 5 wt % such as 0.5 to 1 wt %.

An antiperspirant composition according to the invention comprises an antiperspirant active. Examples of suitable actives include aluminium salts, zirconium salts, aluminium and/or zirconium complexes, for example aluminium halides, aluminium hydroxy halides, zirconyl oxyhalides, zirconyl hydroxyhalides, and mixtures thereof. Specific examples include activated aluminium chlorohydrate, aluminium chlorohydrate, aluminium pentachlorohydrate and aluminium zirconiumchlorohydrate. Useful zirconium salts include zirconium hydroxy-chloride and zirconium oxychloride. Other generally used actives will be known to those skilled in the art. Preferred actives include AAZG (Activated Aluminium Zirconium Glycine), ZAG (Zirconium Aluminium Glycine), and AACH (Activated Aluminium Chorohydrate). The antiperspirant active can be present in particulate form or in solution, such as for example in aqueous solution, advantageously 30 to 60% by weight solution.

The amount of antiperspirant active present in the composition according to the invention may be from 1–35% by weight of the composition, preferably from 10–30% by weight and more preferably 20–30% by weight of the composition.

The deodorant compositions according to the invention normally comprise 0.01 to 90% of a deodorant active. The deodorant active used in the cosmetics of the invention can be any deodorant active known in the art such as alcohols, in particular aliphatic monohydric alcohols such as ethanol or propanol, antimicrobial actives such as polyhexamethylene biguanides eg Cosmocil™ or chlorinated aromatics, eg Triclosan™, non-microbiocidal deodorant actives such as triethylcitrate, bactericides and bacteriostatis.

The carrier material for the antiperspirant composition according to the invention can also comprise one or more of volatile carrier fluids, one or more of non-volatile emollients, and one or a combination of thickener and/or structurant materials if required. The carrier material, including, where relevant, carrier materials providing additional properties such as emolliency, can often comprise up to about 90 wt % of the composition, in many instances from 5 to 80 wt % and particularly from 10 to 70 wt %. Where the composition comprises both hydrophylic and hydrophobic phases, the weight ratio of the two phases is often in the range of 10:1 to 1:10. Aerosol compositions according to the present invention can conveniently be obtained by introducing a base formulation as described herein that is free from propellant and at least 0.7 times and often 1.5 to 20 times its weight of propellant into a suitable aerosol dispenser.

The antiperspirant or deodorant composition can comprise a mixture of particulate solids or a suspension of solids in a liquid medium, which can be thickened to reduce the rate of segregation or structured to produce a cream (soft solid) or solid. Alternatively the composition can comprise a mixture of liquid constituents, including a solution of an active in a carrier, such a composition often adopting the form of an oil in water or water in oil emulsion, which may be thickened or gelled.

The carrier material, which may be a fluid or a mixture of fluids, is often selected according to the physical form of the cosmetic composition, e.g. volatile low viscosity silicones, low molecular weight hydrocarbons, alcohols with the exception of ethanol, and water, and can be selected by those skilled in the art to provide appropriate physical and sensory properties for the product.

Volatile silicones are usually selected from cyclic polysiloxanes containing from 3 to 8 dialkylsilicone groups, especially dimethylsilicone groups and particularly 4 or 5 dimethylsilicone groups. Other useful volatile silicones can comprise linear polysiloxanes, preferably containing 4 or 5 alkylsiloxane groups, including terminal groups. Low molecular weight liquid hydrocarbons can comprise paraffin oils. Suitable alcohols can comprise monohydric alcohols, such as C3 to C10 aliphatic alcohols, dihydric alcohols such as glycol or propylene glycol or polyhydric alcohols such as glycerol or sorbitol. Carrier materials can provide additional desirable properties, such as polyhydric alcohols for example glycerol can act as a moisturising agent and volatile cyclomethicones can act as emollients.

The non-volatile emollient, if used in the composition, may consist of a single emollient compound or a mixture of emollients, and can typically include fatty acids and fatty alcohol esters, slightly water soluble ethers and alcohols, hydrocarbons, water insoluble ethers, mineral oils and polyorganosiloxanes, and mixtures thereof.

Non-volatile silicones are often polyalkylsiloxanes, polalkylarylsiloxanes or polyethersiloxanes having a viscosity of above 10 mPa.s, such as up to about $5 \times 10^6$ mPa.s at 25° C., including polymethylphenylsiloxanes or dimethylpolyoxyalkylene ether copolymers.

Emollient aliphatic esters, often containing from about 12 to 25 carbons, and preferably one substituent containing a chain of at least 12 carbons examples include cetyl palmitate, butyl myristate, glyceryl stearate and propylene glycol monolaurate. The composition cam comprise a liquid aliphatic ether which can provide emolliency, such as ethers derived from polyalyene glycols and a a low weight (eg up to C6) alcohol, such as polypropylene glycol (10–15) butyl ether.

The total amount of emollient materials within the composition, excluding borage oil, is often within the range of from 1 to 70 wt %.

The thickening or structurant agent, when required, is selected according to the product form of the cosmetic composition. The thickening or structuring agent can be organic (monomeric or polymeric) or inorganic and is usually chosen depending on the physical nature of the liquid phase to be thickened or structured, such as whether it is hydrophobic or hydrophylic. The amount is normally slelected in order to attain the desired viscosity or the liquid or cream or desired resistance to penetration of a solid in accordance with the present invention. It can be any of a number of materials, including, for example, waxy structurants for a hydrophobic composition or phase including hydrogenated vegetable oil, hydrogenated castor oil, fatty acids, such as hydroxystearic acid, beeswax, paraffin wax, microcrystalline waxes, silicone wax, and fatty alcohols, such as stearyl alcohol. Polymeric materials for thickening include polymers such as polyamides, hydroxypropylcellulose, and natural or synthetic gums, such as polyglycerides including agar, agarose, pectin, or guars or mixtures or combinations thereof. A further class of polymers that is particularly directed to structuring an oil phase containing a silicone oil comprises polysiloxane elastomers. Suspending agents such as silicas or clays such as bentonite, montmorillonite or hectorite, including those available under the trademark Bentone can also be employed to thicken liquid composiitons according to the invention. The composition can be thickened with non-polymeric organic gellants, including selected dibenzoyl alditols (eg dibenzoyl sorbitol) or selected n-acyl amino derivatives (eg N-acyl glutamide derivatives) or selected hydroxyfatty acids (eg 12-hydroxystearic acid) or selected sterols (eg cholesterol) or selected secondary amides of di or tri basic carboxylic acids, (eg 2-dodecyl-N,N'-dibutylsuccinimide) by themseleves or in combination.

The amount of structurant or thickening agent that should be employed in the invention compositions will depend upon the viscosity of a fluid formulation or extend of hardness of a solid formulation that the producer wishes to attain. The amount to be employed will in practice also vary depending on the chemical nature of rthe structurant or thickening agent. In many instances, the amount of structurant or thickening agent will be selected in the range of from 0.1 to 20 wt %, and particularly from 1 to 15 wt %.

The composition according to the invention can optionally comprise other ingredients, in addition to those already identified, depending on the nature and form of the finished product.

Other ingredients common to the art can also be included in the compositions according to the invention. These include surfactants, fillers, fragrances, preservatives and colouring agents for example. These ingredients are selected according to the physical and chemical from of the cosmetic composition.

Surfactants can comprise optionally up to 25%, more commonly up to 5% by weight of the total product, and are particularly useful in formulating emulsion antiperspirant or deodorant compositions, for example for use as pump spray or roll-on formulations. However for other product types, it is preferred that the composition contains less than about 8% by weight of surfactants. Non-ionic surfactants are particularly preferred. It is often convenient to select a mixture of surfactants, such as one having a comparatively high HLB value, eg 8 to 18, and one having a comparatively low HLB value, eg 2 to 8, which can be introduced in suitable relative proportions to to attain an average HLB value of about 6 to 12.

Many suitable nonionic surfactants are selected from nonionic esters, ethers or amine oxides having an appropriate HLB value. Many preferred ionic surfactants comprise a polyoxyalkylene moiety, especially a polyoxyethylene moiety eg 2 to 80, especially 5 to 60 oxyethylene units, or possibly with a polyoxypropylene content, to provide hydrophilicity. Other moieties providing huydrophlicity include polyhydric alcohols such as sorbitol or glycerol. The hydrophobic moiety is commonly derived from aliphatic alcohols or acids or amines containing about 8 to 50 carbons and particularly 10 to 30 carbons. Examples of suitable nonionic surfactants include ceteareth-10 to -25, ceteth-10-25, steareth-10-25, and PEG-15-25 stearate or distearate. Other suitable examples include C10–C20 fatty acid mono, di or tri-glycerides. Further examples include C18–C22 fatty alcohol ethers of 1–5 polyethylene oxides (8 to 12 EO).

Examples of surfactants which typically have a low HLB value, and often of from 2 to often comprise mono or possibly di fatty acid esters of polyhydric alcohols such as glycerol, sorbitol, erythritol or trimethylolpropane, including cetyl, stearyl arachidyl and behenyl. Other examples include monoglycerides of palmitic or stearic acid, sorbitol mono or diesters of myristic palmitic or stearic acid, and trimethylolpropane monoesters of stearic acid.

Fillers can comprise up to about 20%, more commonly up to 10% of the total product and are normally less costly that the essential components of the invention, thereby reducing overall cost. Suitable fillers include aluminium stearate, aluminium tri-stearate, calcium stearate, talc or finely divided polyethylene, an example of which is ACUMIST B18.

Fragrances, when present, typically comprise up to about 1% of the total product.

Colouring agents and preservatives can be added as desired. Other optional ingredients are other cosmetic adjuncts conventionally employed in antiperspirant or deodorant products.

The ingredients which can optionally be present in the composition carrier can conveniently form the balance of the composition.

Propellants commonly employable in aerosol compositions herein comprise hydrocarbons (or much less desirably halohydrocarbons) having a boiling point of below 10° C. and especially those with a boiling point below 0° C. It is especially preferred to employ liquified hydrocarbon gasses, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

The composition according to the invention can take any form of a product suited to or adapted for topical application to human skin, and is usually contained in a suitable holder or dispenser to enable it to be applied to the area of the skin, particularly the underarm, where control of perspiration and deodorancy is required.

EXAMPLE 1

Twenty healthy male/female volunteers, who were between the ages of 18 and 55, were recruited for each test.

Test Patches

Patches consisted of a compartmented strip of Al-test units (Finn chambers of 0.8 cm internal diameter) fixed onto 5 cm wide occlusive Scanpor tape manufactured by Norgesplaster, Norway. Ten compartments were used in these studies to contain the ten test samples.

Test Procedure

The protocol adopted for these studies were of the double-blind, within subject comparison type. They were conducted on twenty healthy volunteers per test.

It is a safety clearance condition of forearm patch testing that panellists have a "rest period" of 3 weeks before a forearm site can be repatched.

Protocol

Patches were prepared by placing a small amount of petroleum jelly (White Petroleum Jelly ex. Boots) in the bottom of each test chamber, followed by a filter paper onto which the test material was dosed. One drop of each test product was dosed in turn onto a filter paper using a Pastette alpha 1.0 ml plastic pipette supplied by Orme scientific. This constituted on average a dose of approximately 0.02 g. In the case of the aerosol product it was sprayed directly on to the filter paper (in a ventilated spray booth) and the filter paper was then inserted into the appropriate Finn chamber immediately before patching (the average dosage of the aerosol was estimated from the results from 20 such saturated filter papers. Products were randomised across patch sites. Panellists were instructed to keep patches clean and dry when in place.

Panellists reported on the Monday morning of the test week when they had a patch applied to clear skin of one inner forearm. These patches remained in place for 24 hours when panellists again reported and the patch was removed. They returned six hours later for assessment of each of the patch sites. Fresh patches, using the same product randomisation, were applied. These patches remained in place for 18 hours, panellists again reported and the patch was removed; again the patches were graded six hours later. This repatching/grading was repeated on Thursday and Friday. A final recovery reading was performed on the following Tuesday morning—i.e. 5 gradings were performed in total. The readings six hours after the final patch removal were of most interest. One potential issue with this protocol (highlighted during the safety clearance process) was 'tape reaction' due the multiple application and removal of tape from the same forearm site. Therefore the degree of tape reaction was also recorded using the same grading scale as used for the patch sites.

The score for each test was graded according to the Patch Grading Scale. The score for each sample was averaged to produce a final score.

| Patch Grading Scale | |
|---|---|
| Grade | Description |
| 0.0 | No apparent cutaneous involvement. |
| 0.5 | Faint, barely perceptible erythema or slight dryness |
| 1.0 | Faint but definite erythema, no eruptions broken skin or no erythema but definite dryness; may have epidermal fissuring. |
| 1.5 | Well defined erythema or faint papules with definite dryness, may have epidermal fissuring. |
| 2.0 | Moderate erythema, may have very few papules or deep fissures, moderate to severe erythema in the cracks. |

Patch Grading Scale

| Grade | Description |
|---|---|
| 2.5 | Moderate erythema with barely perceptible oedema or severe erythema not involving a significant portion of the patch (halo effect around the edges), may have a few papules or moderate to severe erythema. |
| 3.0 | Severe erythema (beet redness), may have generalized papules or moderate to severe erythema with slight oedema (edges well defined by raising). |
| 3.5 | Moderate to severe erythema with moderate oedema (confined to patch area) or moderate to severe erythema with isolated eschar formations or vesicles. |
| 4.0 | Generalized vesicles or eschar formations or moderate to severe erythema and/or oedema extending beyond the area of the patch. |

Results

| Sample | Description | Score |
|---|---|---|
| 1 | Standard AP Stick([1]) | 0.79 |
| 2 | Standard AP Stick + 17.5% Borage Seed Oil | 0.35 |
| 3 | Standard AP Aerosol([2]) | 0.79 |
| 4 | Standard AP Aerosol + 6.4% Borage Seed Oil | 0.26 |

Standard statistical analyses showed that sample 2 was significantly milder than sample 1 and that sample 4 was significantly milder than sample 3.

EXAMPLE 2

The following is an antiperspirant stick formulation according to the invention. It-can be made by standard methods known in the art.

| Stick Example | |
|---|---|
| AZAG | 24% |
| Estol EO4DS | 1% |
| Caster wax | 4% |
| Lorol C18 deo | 14% |
| Talc | 3.2% |
| Perfume | 1% |
| Volatile Silicone DC345 | 35.3% |
| Borage Seed Oil | 17.5% |

(1) Comprising 24% AZAG; 1% ESTOL EO4DS; 4% Casterwax; 14% Lorol $C_{18}$ deo; 3.2% Talc; 1% perfume; and 52.8% volatile silicone DC345.

(2) Comprising 10% AACH; 1% Bentone 38; 1.0% perfume; 13% volatile silicone Q2 1465 and 75% propellant.

EXAMPLE 3

The following is an antiperspirant aerosol formulation according to the invention. It can be made by standard methods known in the art.

| Aerosol Example | |
|---|---|
| AACH | 10.0% |
| Bentone 38 | 1.0% |
| Perfume | 1.0% |
| Volatile Silicone Q2 1465 | 6.6% |
| Borage Seed Oil | 6.4% |
| Propellant CAP 40 | 75% |

What is claimed is:

1. An antiperspirant or deodorant cosmetic composition suitable for topical application to the human skin, comprising:

i. an antiperspirant or deodorant active;

ii. a carrier for the antiperspirant or deodorant active; and iii. borage seed oil in an effective amount from at least about 0.05% to 20% bt weight to reduce or eliminate skin irritation or sting caused by the co-components of said composition.

2. A composition according to claim 1 characterised in that it comprises from 0.5 to 10% by weight of the borage seed oil.

3. A composition according to claim 1 characterised in that it comprises from 10 to 30% by weight antiperspirant active.

4. A composition according to claim 1 characterised in that the antiperspirant active contains zirconium.

5. A composition according to claim 1 characterised in that it comprises a volatile silicone carrier.

6. A composition according to claim 1 characterised in that it comprises a structurant or thickening agent in a concentration sufficent to produce a stick or cream.

7. A composition according to claim 5, wherein said volatile silicone carrier is present in an amount of from 10 to 70 wt. %.

* * * * *

UNITED STATES PATENT AND TRADEMARK OFFICE
CERTIFICATE OF CORRECTION

PATENT NO.    : 6,086,887
DATED         : July 11, 2000
INVENTOR(S)   : Parrott

It is certified that error appears in the above-identified patent and that said Letters Patent is hereby corrected as shown below:

<u>Column 8,</u>
Line 31, after 20% change bt to -- by --.

Signed and Sealed this

Twenty-fifth Day of September, 2001

Attest:

NICHOLAS P. GODICI
Attesting Officer           Acting Director of the United States Patent and Trademark Office